United States Patent [19]

Larimore et al.

[11] 4,273,135

[45] Jun. 16, 1981

[54] BIOMEDICAL ELECTRODE

[75] Inventors: Franklin C. Larimore, Shoreview; Steven M. Heilmann, North St. Paul, both of Minn.

[73] Assignee: Minnesota Mining and Manufacturing Company, St. Paul, Minn.

[21] Appl. No.: 940,735

[22] Filed: Sep. 8, 1978

Related U.S. Application Data

[63] Continuation-in-part of Ser. No. 825,870, Aug. 19, 1977, abandoned.

[51] Int. Cl.$^3$ .............................................. A61B 5/04
[52] U.S. Cl. .................................... 128/640; 128/802
[58] Field of Search ................... 128/640, 641, 303.13, 128/798, 802, 803

[56] References Cited

U.S. PATENT DOCUMENTS

| 2,555,037 | 5/1951 | Jensen | 128/803 X |
|---|---|---|---|
| 3,911,906 | 10/1975 | Reinhold, Jr. | 128/641 |
| 3,946,730 | 3/1976 | Monter | 128/641 |
| 3,989,050 | 11/1976 | Buchalter | 128/419 R |
| 3,993,049 | 11/1976 | Kater | 128/640 |
| 3,998,215 | 12/1976 | Anderson et al. | 128/641 |
| 4,002,221 | 1/1977 | Buchalter | 128/660 X |
| 4,066,078 | 1/1978 | Berg | 128/641 |
| 4,125,110 | 11/1978 | Hymes | 128/641 |

Primary Examiner—Lee S. Cohen
Attorney, Agent, or Firm—Cruzan Alexander; Donald M. Sell; Carolyn A. Bates

[57] ABSTRACT

An essentially dry, disposable biomedical electrode is disclosed having an improved electrically-conductive material at the interface between the electrode and the skin. The conductive material consists essentially of a cohesive, conformable, nonionic hydrophilic synthetic polymer.

13 Claims, 2 Drawing Figures

BIOMEDICAL ELECTRODE

This application is a continuation-in-part of application Ser. No. 825,870, filed Aug. 19, 1977, now abandoned.

This invention relates to disposable electrodes, often termed "biomedical" electrodes, for establishing an electrical connection between the skin of the human anatomy and an electromedical apparatus, such as a high impedance electromyograph, electrocardiograph, electrostimulator for pain relief, and the like. More particularly it relates to so called "dry" bioelectrodes which do not require the use of messy creams or gels to enhance conductivity between the skin and the electrode plate.

A variety of disposable biomedical electrodes are known in the art. Generally, they comprise a metallic electrode plate adapted for connection to a lead wire which is, in turn, attached to the electromedical apparatus. Typically, a paste, cream, or gel which contains ionic material is relied upon to conduct the electric current and improve the electrical connection between the skin of the patient and the electrode plate. An adhesive tape is commonly used to adhere the entire apparatus to the skin. Examples of electrodes of this general type are described in U.S. Pat. Nos. 3,587,565 and 3,805,769.

The conductive pastes, creams, or gels used in these prior art biomedical electrodes are unpleasant to use, sloppy, and often irritating to the skin because of their ionic nature, particularly when the skin is cleaned and abraded prior to application of the electrode. Since these electrodes all contain water as the major ingredient to solvate the ions present and function as a medium through which the solvated ions migrate, they require elaborate packaging to prevent loss of water prior to use. Furthermore, they leave a residue on the skin after removal of the electrode which requires cleanup. A further disadvantage of the electrodes of the conductive paste, cream, and gel types is that they develop an overpotential in defibrillation procedures unless the surface of the electrode plate is of expensive silver/silver chloride.

The messy, unpleasant, and inconvenient nature of electrodes using conductive gels or creams has been somewhat alleviated by impregnating a porous pad with the conductive material as shown, for example, in U.S. Pat. Nos. 3,845,757 and 3,901,218. However, elaborate packaging is still required, and, in use, the gel tends to dry out causing variations in the electrical impedance and subsequent signal quality.

To overcome many of the problems associated with so called "wet" electrodes, biomedical electrodes have been proposed which utilize "dry" conductive material. U.S. Pat. Nos. 3,565,059 and 3,911,906 disclose biomedical electrodes utilizing adhesives impregnated with conductive particles. These adhesives serve the dual purpose of enhancing conductivity with the skin and securing the electrode to the skin. Although avoiding the sloppiness and packaging problems associated with gels and pastes, such electrodes generally do not provide satisfactory electrical connection to the skin because the presence of the conductive filler results in a high signal-to-noise ratio and is deleterious to adhesion. Generally, the use of non-homogeneous conductive formulations in bioelectrodes has been found to give rise to noisy electrical signal. It is speculated that dispersed metal or salt particles in a binder matrix form a discontinuous, electrically conductive path which develops random, non-uniform electrical fields between particles which causes noise.

U.S. Pat. No. 3,993,049 discloses a biomedical electrode having a salt dispersed in an adhesive layer. The adhesive layer secures the electrode to the skin, and the salt serves as the current carrier. Preferably, the salt has a cation of the metal that forms the surface of the electrode plate, e.g., silver halide with a silver electrode plate. It is also preferred to include metal powders in the adhesive or provide a metal screen on which the adhesive is carried. The preferred adhesives are water-soluble. This biomedical electrode requires the addition of extraneous material, i.e., a salt solution and metal powders, into the adhesive layer in order to obtain acceptable electrical conductivity. This increases the possibility of skin irritation as well as the overall cost of the electrode.

Although the predominance of the art in the field of biomedical electrodes as described above is directed to recording electrodes useful in diagnostics, there is an increasing amount of art appearing that describes grounding electrodes and electrodes for electrical stimulation of parts of the anatomy for purposes of aiding in healing of injuries or trauma or the like. For the most part, the variously described grounding and stimulating bioelectrodes are larger in area than the recording electrodes so that greater current densities can be used without burning body tissue. Again, these larger electrodes generally use an electrolyte solution, gel, or paste to provide electrical contact between the body surface and the electrode. Patents describing such electrodes include, for example, U.S. Pat. No. 3,817,252 describing a body conformable electrode utilizing a "diffuser screen" and a conductive paste; U.S. Pat. No. 3,848,600 describing a contoured electrode utilizing an aqueous salt solution containing 0.2 to 8% neutralized mucilage as electrolyte; and U.S. Pat. No. 3,964,477 describing an electrode utilizing a porous silver-silver chloride electrode and an electrolyte solution. All of these electrodes utilize an undesirably messy electrolyte.

Another biomedical electrode used for transcutaneous electrical neutral stimulation which has been called to the applicants' attention utilizes a natural polymer, namely, gum karaya, for securing the electrode to skin. Gum karaya is a complex polysaccharide combined with certain metallic cations, such as sodium, potassium, calcium, or magnesium. The gum does not dissolve but swells in water to a paste-like gel (Kirk-Othmer, Encyclopedia of Chemical Technology, Vol. 10, 1966). Because natural polymers originate in nature where soil and climatic conditions are variable, and the conditions under which they are collected and processed are variable, there is a great inconsistency in the physical and chemical properties of natural polymers and in the amount of impurities present. Such inconsistency leads to variations in the electrical performance of biomedical electrodes made from natural polymers. This variation in electrical performance cannot be tolerated in biomedical electrodes where consistent electrical properties are important. Furthermore, the natural polymers are undesirable because they generally support microbial growth and have the potential for creating adverse skin sensitivities including allergenic and antigenic reactions (Merck Index, 8th Edition, 1969, page 598).

"Dry" stimulation electrodes are also known. U.S. Pat. No. 3,812,861 teaches a grounding electrode consisting of a flexible sheet of paperboard coated on both sides with a conductive foil joined electrically together and a means for tightening the device around a limb. Such electrodes having a metal-to-tissue interface are undesirable because of the bio-incompatability of most metals and the difficulty of obtaining adequate conformability with the body surface. U.S. Pat. No. 3,994,302 describes an implantable stimulating electrode wherein the tissue contacting surface is an ion-exchange resin material, such as, for example, quaternized vinyl pyridine grafted to polyethylene. For use, the electrode may be activated by an aqueous solution. This electrode does not appear to be useful on the surface of the skin.

According to the present invention, it has been discovered that the presence of salts or dispersed conductive matter in the interface material between the skin and the electrode plate is not a requirement for a workable biomedical electrode. It has further been discovered that certain non-ionic hydrophilic synthetic polymers can function as effective electrically conductive materials in biomedical electrodes.

According to the present invention there is provided an improved, essentially dry, disposable biomedical electrode comprising an electrode plate having on one surface thereof means for electrical connection to an electro-medical apparatus and on the opposite, body contacting surface thereof, an electrically conductive material wherein the electrically conductive material consists essentially of a non-irritating, conformable, cohesive, non-ionic synthetic hydrophilic polymer. The biomedical electrode of the invention has an impedance value of 500 Kohms or less at a frequency of 10 Hertz.

The dry bioelectrode of the invention offers several advantages over conventional prior art electrodes. Since major amounts of water are not required, the need for expensive electrode packaging and other measures designed to insure retention of water are no longer necessary. No packaging is necessary other than a covering to protect the adhesive surface. Application of the electrode is dry, not sloppy or messy, and when the electrode is removed from the skin of a patient no messy residue remains on the skin. The skin may be prepared with either water or a normal saline solution instead of alcohol which tends to be irritating. There is no need to wait for the skin to dry completely before attaching the electrode because adhesion of the electrode to the skin is enhanced somewhat by dampening the skin. The electrode can be made smaller in diameter and thickness than currently available disposable electrodes thus improving comfort and convenience, particularly in long-term monitoring. Additionally, no costly surface treatment of the electrode plate is required in order to render it suitable for use in connection with defibrillation procedures.

The term "conformable" as used herein refers generally to the compliance of the conductive material. It must be sufficiently compliant to conform to the surface of the skin beneath the electrode plate to provide a high surface area of contact between the skin and the electrode plate. The important conformability requirement for materials used according to the present invention is generally satisfied by Williams Plasticity values (as described in U.S. Pat. No. 3,725,121) between 0.5 to 4.0 millimeters for thermoplastic formulations. When an interpolymer has been subsequently crosslinked by one of a variety of known procedures to improve its cohesive properties, the crosslinking may render the formulation insoluble and non-flowing. Such materials cannot be evaluated by the Williams Plasticity measurement which requires flow. A description of glass transition temperature is helpful to distinguish suitably conformable materials of this type. A general account of glass transition temperatures and physical characteristics is found in J. D. Ferry's text entitled "Viscoelastic Properties of Polymers" (Wiley: New York, Chapter 2 (1970)). Generally, crosslinked polymers having a glass transition temperature between $-20°$ to $-95°$ C. are suitably conformable.

The term "non-ionic hydrophilic polymer" as used herein refers to a large molecule built up by the repetition of a sufficient number of small chemical units, of which at least fifteen mole percent are water-soluble, to provide cohesive and film-forming properties, generally having a weight-average molecular weight of at least about 10,000 and preferably 100,000. The polymer does not contain ionic groups.

The term "synthetic" as used herein refers to those hydrophilic polymers which have been synthesized in contrast to those polymers which are collected in nature and simply processed to remove foreign matter such as dirt, leaves, and insects and on which no chemical reaction has been performed. The term "synthetic" also includes polymers which have been made by chemical modification of a natural polymer to alter its chemical structure and standardize its chemical and physical properties.

The term "cohesive" refers to the internal integrity of the conductive material. Generally, the conductive material is film-forming and must be more cohesive than adhesive to the skin so that, when the electrode is removed from the skin, the conductive layer remains intact and does not leave an objectionable residue on the skin.

Conformable, non-ionic hydrophilic polymers suitable for use as the electrically conductive material of the biomedical electrode of the invention can be any dermally-nonirritating, cohesive, film-forming synthetic hydrophilic polymer selected from the following classes:

A. non-ionic water-soluble polymers of substantially all water soluble monomers;

B. non-ionic water-soluble interpolymers of water-soluble monomers and water-insoluble monomers;

C. non-ionic hydrophilic water-insoluble interpolymers of water-soluble monomers and water-insoluble monomers that contain at least 15 mole percent of interpolymerizable water-soluble monomers.

The polymers of Class A, non-ionic water-soluble synthetic polymers, are well known and a great many have been prepared. All are suitable for use in the invention if they are film-forming; generally, a weight-average molecular weight of about 10,000 will make them film-forming. Examples of Class A polymers are:

hydroxyalkylcellulose such as 2-hydroxyethylcelluloses; and synthetic polymers of water-soluble monomers.

Water-soluble monomers which can be homopolymerized or interpolymerized with other members of the series to give Class A water-soluble non-ionic polymers in accordance with well known methods include the following vinyl monomers:

acrylic acids such as acrylic and methacrylic acids;

olefinic polycarboxylic acids such as maleic acid, fumaric acid, itaconic acid, aconitic acid, and citraconic acid;

acrylamides such as acrylamide, methacrylamide, N-alkylacrylamides such as N-methylacrylamide, N-butylacrylamide, and N-methylmethacrylamide;

vinyl alcohol, obtained by polymerization of vinyl acylates, such as vinyl acetate and hydrolysis of the resulting polymer;

N-vinyl lactams such as N-vinyl pyrrolidone;

2-vinyl imidazoline as disclosed in U.S. Pat. No. 3,557,061;

2-vinyl tetrahydropyrimidine as disclosed in U.S. Pat. No. 3,557,061;

vinyl pyridines such as 2-, 3- and 4-vinyl pyridine;

aminoalkylacryl compounds, e.g., aminoalkylacrylamides such as N-(2-dimethylaminoethyl)acrylamide, N-(2-dimethylaminoethyl)acrylamide, N,N-bis(2-dimethylaminoethyl)acrylamide and N-(4-dimethylamino cyclohexyl)acrylamide and aminoalkylacrylates such as 2-dimethylaminoacrylates acrylate, 2-dimethylaminopropyl acrylate, and 3-diethylaminopropyl methacrylate;

vinyl ethers such as vinyl methyl ether;

Still other monomers that may be polymerized to Class A water-soluble polymers are ethylene oxide and ethyleneimine.

The non-ionic hydrophilic interpolymers of Class B result from interpolymerization of major amounts of addition-polymerizable, water-soluble monomers listed above with minor amounts of non-ionic addition-polymerizable, water-insoluble monomers which include, but are not limited to:

acrylate esters such as methyl acrylate, methyl methacrylate, butyl acrylate, iso-octyl acylate, 2-ethylhexyl acrylate, dodecyl methacrylate, octadecyl methacrylate, and cyclohexyl acrylate;

vinyl ethers such as 2-ethylhexyl vinyl ether, decyl vinyl ether, and octadecylvinyl ether;

vinyl acylates such as vinyl acetate, vinyl butyrate, and vinyl dodecanoate;

olefins such as ethylene, propylene, styrene, α-methylstyrene, 4-chlorostyrene, iso-butylene, and vinylcyclohexane;

olefinic polycarboxylic acid esters such as dimethyl maleate, dimethyl fumarate, and diethyl itaconate; and vinyl halides such as vinyl chloride and vinylidene dichloride.

As is apparent to one skilled in the art, the specific minimum concentration of the water-soluble monomers necessary to confer water-solubility on the interpolymer can not be given since that value will vary considerably depending on the nature of both the water-soluble and the water-insoluble monomers.

The preferred hydrophilic polymers of the invention are those of Class C, non-ionic hydrophilic water-insoluble interpolymers. The Class B interpolymers discussed above represent a special kind of Class C interpolymers with the former being differentiated by their solubility in water. The Class C interpolymers, though not water-soluble, are hydrophilic and are prepared using the same addition-polymerizable non-ionic water-soluble and water-insoluble monomers discussed above. The advantage attributable to the Class C materials is that with water-soluble monomer levels greater than 15 mole percent impedance values less than the impedance limit of 500 Kohms (judged to represent a practical upper limit with state of the art electrocardiography and biofeedback electrical instruments) are achieved and pressure sensitive adhesive performance is optimum. Materials that are pressure sensitive adhesives are especially preferred materials of the invention because no additional means of securing the electrode to the skin is necessary. Pressure sensitive adhesives are well known in the art, and are best described as possessing a balance of four properties—adhesion, cohesion, stretchiness, and elasticity—as discussed, for example, in U.S. Pat. No. Re. 24,906. This balance of properties is most generally accomplished by the interpolymerization of monomers which if homopolymerized would yield a polymer of relatively high glass transition temperature (about 80° C.) or so-called "hard" monomers with monomers which if homopolymerized would yield a polymer of relatively low glass transition temperature (about 25° C.) or so-called "soft" monomers. The "hard" monomers employed in the present invention are generally the non-ionic water-soluble, addition-polymerizable monomers hereinbefore described above while the "soft" monomers are the above described non-ionic water-insoluble, addition-polymerizable monomers, especially those that contain relatively large alkyl residues containing about 4 to 12 carbon atoms. Especially preferred "soft" monomers include the alkyl acrylate and methacrylate esters and the alkyl vinyl ethers. The "hard" and "soft" monomer charges are manipulated so that an interpolymer with a glass transition temperature less than −25° C. is obtained.

When the previously described polymers alone are not sufficiently conformable under use conditions, they can generally be brought within the prescribed limits by plasticization. The interpolymerization of "hard" and "soft" monomers discussed above with the Class B and Class C materials is herein termed "internal" plasticization. Especially with the Class C materials, this interpolymerization of the "soft" monomers that have large bulky, pendant, alkyl substituents with the "hard" monomers many impart sufficient fluidity to the copolymer. For example, 85 molar parts of iso-octyl acrylate interpolymerized with 15 molar parts of acrylic acid results in an interpolymer that exhibits a Williams Plasticity value of 2.5 millimeters. The iso-octyl acrylate is the "soft" monomer internally plasticizing the "hard" acrylic acid which by itself as a homopolymer is so brittle it cannot be evaluated using the Williams Plasticity measurement.

Alternatively, plasticization of polymers and interpolymers of the invention can be accomplished by adding a more "fluid" ingredient to the polymer or interpolymer. This procedure is herein termed "external" plasticization. Generally, it is desirable that this external plasticizing agent be compatible with the polymer. The external plasticizer can be any material that will result in transforming a brittle polymer into a conformable one such that the above described Williams Plasticity values and/or glass transition temperature criteria are satisfied. The effectiveness of this technique is demonstrated by producing a Williams Plasticity value of 2.5 millimeters with poly(acrylic acid) by the addition of 85 parts (based on 100 parts poly(acrylic acid)) of glycerol.

Suitable "external" plasticizers include poly(hydroxyalkanes) such as glycerol, poly(oxyalkylene) alcohols such as poly(oxypropylene) glycol, and the like.

It is also contemplated within the scope of the invention to tackify the formulations herein described where necessary, especially to prepare a pressure sensitive adhesive formulation which is a preferred embodiment of the invention.

Suitable tackifiers for all the classes of the invention are the derivatives of naturally occurring acid resins such as abietic acid. The acid or its hydrogenated form can be reacted with bases to form water-soluble tackifying agents for the water-soluble Class A and Class B polymers and interpolymers, respectively, or the acid can be esterified or reduced to suitable water-insoluble tackifiers for the Class C materials. Many other tackifiers are commercially available and suitable for use especially with the Class C materials which are the preferred materials of the invention.

Examples of preferred electrically conductive nonionic polymers for use in the electrode of the invention are listed in the following Table I. All ratios are molar ratios.

TABLE I

Preferred Class A Polymers

Poly(acrylic acid)
Poly(methyacrylic acid)
Poly(vinyl alcohol)
Poly(vinylpyrrolidone)
Poly(vinyl methyl ether)
Copoly(methyl vinyl ether: maleic acid) (50:50)
Poly(acrylamide)
Poly(oxyethylene)
Poly(ethyleneimine)

Preferred Class B Interpolymers

Copoly(vinyl acetate:vinyl alcohol) (30:70)
Copoly(n-butyl acrylate:acrylic acid) (5:95)
Copoly(2-ethylhexyl methacrylate:methacrylic acid) (2:98)

Preferred Class C Interpolymers

Copoly (iso-octyl acrylate:acrylic acid) (61:39)
Copoly (iso-octyl acrylate:acrylic acid) (48:52)
Copoly (butyl acrylate:itaconic acid) (67:33)
Copoly (lauryl methacrylate:methacrylic acid) (34:66)
Copoly (vinyl acetate:vinyl alcohol) (70:30)
Copoly (vinyl chloride:vinyl alcohol) (60:40)
Copoly (ethylene:vinyl alcohol) (60:40)
Copoly (butyl acrylate:3-dimethylaminopropylacrylamide) (60:40)

DESCRIPTION OF THE DRAWINGS

Further understanding of the invention will be facilitated by reference to the accompanying drawings wherein:

In FIGS. 1 and 2 electrode 10 comprises an electrode plate 12 constructed from an electrically conductive material such as stainless steel, silver, nickel or the like, compressed carbon or graphite, or a metal coated plastic, fabric, or conductive plastic material. The electrode plate has means associated therewith for electrical connection to a lead wire which is, in turn, connected to an electromedical device. In electrode 10 the means for electrical connection to a lead wire are illustrated by connector stud 14, a vertical extension of electrode plate 12. Connector stud 14 is adapted to fit a female receptor of a connector. The skin-contacting surface of electrode plate 12 is coated with a layer 18 of conductive material as hereinbefore defined. Layer 18 is generally between 25 and 100 microns thick. Overlying the upper surface of the electrode plate and extending outward from the periphery thereof is a patch of adhesive tape 20. Adhesive tape 20 aids in holding the electrode securely to the skin of the patient. In the preferred embodiments of the invention, the conductive material of layer 18 is sufficiently adhesive to assist in holding the electrode to the skin. Because layer 18 is conformable and generally tacky, good electrical connection between the electrode plate and the skin is provided without the need for a large and bulky piece of adhesive tape as is required in many prior art disposable electrodes. Thus, the electrode of the present invention can be made smaller and is easier to handle. The side of layer 18 opposite that secured to the electrode plate is optionally provided with a protective release liner 22. Release liner 22 protects the conductive layer 18 and the adhesive side of patch 20 from contamination prior to use.

Figure 1:
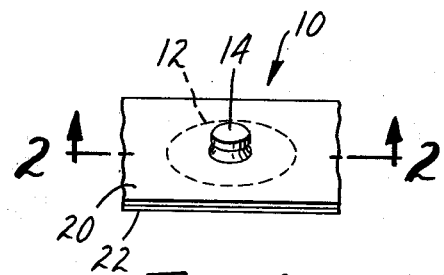
FIG. 1 is a top perspective view of a typical disposable biomedical electrode according to the invention.
Figure 2:
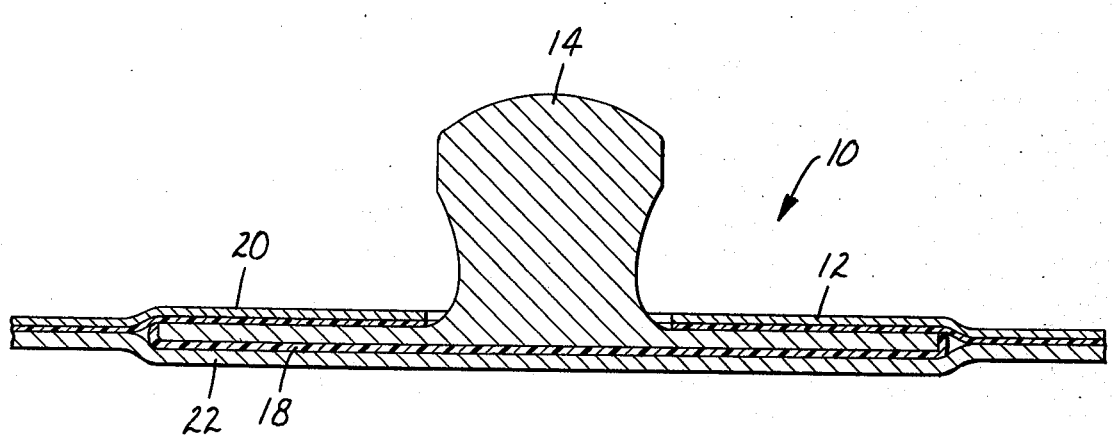
FIG. 2 is an enlarged cross-sectional view of the electrode taken along line 2—2 of FIG. 1.

It will be apparent to one skilled in the art that the biomedical electrode of the invention may be constructed in various ways. The embodiment illustrated is merely an example of a typical disposable electrode of the recording type. Electrodes used for other purposes, e.g., for stimulation, for grounding in electrosurgery, and for biofeedback, have different requirements and must be constructed to meet those requirements. All types of noninvasive electrodes which utilize the conductive material of the invention at the interface of the electrode and the skin are contemplated within the scope of the invention.

The invention is further illustrated by the following non-limiting examples.

EXAMPLE 1

Preparation of Poly(acrylic acid) (100 parts) and glycerol (60 parts)

Poly(acrylic acid) having a weight-average molecular weight of about 120,000 (5.29 grams polymer in 25.3 grams water) and glycerol (3.18 grams) were mixed thoroughly.

Electrodes were made by coating the plasticized polymer onto nickel plated discs having an area of approximately 127 mm$^2$ and air drying overnight. A polymer layer having a thickness of 75±25 microns was obtained.

The impedance value of the electrodes was obtained by applying an electrode to the skin of the inner forearm of a human male subject. The skin site was prepared by lightly abrading with a #220 open coat aluminum oxide sandpaper, and the abraded area was wiped with a 2 in. (5 cm)×2 in. (5 cm) 12 ply gauze sponge dampened with normal saline solution. The electrode was attached to the skin site while it was still visibly wet with a piece (2.5 cm by 4 cm) of 3M Brand Micropore Tape.

Impedance measurements were made using the method reported by Spach et al., *Circulation* 34, 649–656 (1966)). All impedance measurements were made at a frequency of 10 Hertz. The electrode was found to have an impedance value of 20 Kohms. Other electrodes were prepared and tested using water-soluble polymers as the conductive material. In some cases the skin was prepared with water alone instead of the saline solution generally used. The results are summarized in the following table:

| EX. | CONDUCTIVE MATERIAL | SKIN PREPARATION | IMPEDANCE (KOHMS) |
|---|---|---|---|
| 1 | Poly(acrylic acid) + 60% glycerol | Saline | 20.0 |
| 1a | Poly(acrylic acid) + 60% glycerol | Water | 20.0 |
| 2 | Poly(vinyl alcohol) | Saline | 3.5 |
| 2a | Poly(vinyl alcohol) | Water | 98.0 |
| 3 | Poly(vinyl alcohol) +100% glycerol | Saline | 2.0 |
| 3a | Poly(vinyl alcohol) + 100% glycerol | Water | 198.0 |
| 4 | Poly(acrylic acid) + 400% glycerol | Saline | 7.0 |
| 5 | Copoly(methyl vinyl ether:maleic acid) (50:50) + 150% glycerol | Saline | 6.0 |

The conductive materials of Examples 1–5 were all tacky formulations under use conditions except for Examples 2 and 3 which were readily conformable but not tacky.

EXAMPLE 6

Preparation of Copoly(iso-octyl acrylate-acrylic acid) (78:22)

Iso-octyl acrylate (252.0 grams), acrylic acid (28.0 Grams), and azobis(iso-butyronitrile) (0.700 gram; 0.25 weight percent based on monomer) were dissolved in acetone (420 grams; monomer solids was 40.00 weight percent) in a one liter amber glass bottle. The resulting solution was sparged briefly with nitrogen to remove dissolved oxygen, sealed, and heated with agitation at 53° C. for 24 hours. The resulting copolymer solids was 38.3 weight percent, and the inherent viscosity in tetrahydrofuran at 30° C. (0.15 gram copolymer per 100 grams solvent) was 1.71.

An electrode was prepared using the copolymer following the method described in Example 1. The electrode was tested and found to have an impedance value of 160 Kohms.

Using the method of Example 6, other conductive materials were prepared and incorporated into electrodes. These electrodes are summarized in the following table:

TABLE II

| EX. | FORMULATION | IMPEDANCE (Kohms) |
|---|---|---|
| 7 | Copoly(iso-octyl acrylate:acrylic acid) (86:14) | 4200 |
| 8 | Copoly(iso-octyl acrylate:acrylic acid) (61:39) | 78 |
| 9 | Copoly(iso-octyl acrylate:acrylic acid) (48:52) | 43 |
| 10 | Copoly(butyl acrylate:itaconic acid) (67:33) | 18 |
| 11 | Copoly(lauryl methacrylate: methacrylic acid) (34:66) | 11 |

EXAMPLE 12

Preparation of Copoly(vinyl acetate-vinyl alcohol) (54:46) (100 Parts) and Glycerol (100 Parts)

Copoly(vinyl acetate:vinyl alcohol) (54:46) (commercially available from Wacker Chemie) (6.3 grams) and glycerol (6.3 grams) were dissolved in 56.7 grams of isopropanol-water (50:50 w/w).

The sample when coated, dried, and evaluated as described in Example 1 produced an impedance value of 26 Kohms. The dry material was a tack-free, conformable film.

What is claimed is:

1. In an essentially dry disposable biomedical electrode comprising an electrode plate having an upper surface and a lower body-contacting surface, said upper surface having means for electrically connecting said electrode plate to a lead wire, and a conductive material on said body-contacting surface of said electrode plate for enhancing electrical connection with the skin, the improvement wherein said conductive material consists essentially of a dermally nonirritating, conformable, cohesive, non-ionic synthetic hydrophilic polymer containing at least 15 mole percent of a water-soluble monomer, said electrode having an impedance of 500 Kohms or less at a frequency of 10 Hertz.

2. The electrode according to claim 1 wherein said polymer is selected from the group consisting of:
   (A) water-soluble non-ionic polymers of substantially all water soluble monomers;
   (B) non-ionic water-soluble interpolymers of water-soluble monomers and water-insoluble monomers; and
   (C) non-ionic water-insoluble interpolymers of water-soluble monomers and water-insoluble monomers that contain at least 15 mole percent of water-soluble monomers.

3. The electrode according to claim 2 wherein said polymer is plasticized.

4. The electrode according to claim 3 wherein said polymer is plasticized with glycerol.

5. The electrode according to claim 2 wherein said polymer is a water-soluble polymer of substantially all water-soluble monomers.

6. The electrode according to claim 5 wherein said polymer is selected from the group consisting of polyacrylic acid and polyvinyl alcohol.

7. The electrode according to claim 6 wherein said acrylic acid polymer is plasticized with glycerol.

8. The electrode according to claim 2 wherein said polymer is a water-insoluble interpolymer of water-soluble monomers and water-insoluble monomers that contain at least 15 mole percent of water-soluble monomers.

9. The electrode according to claim 8 wherein said water-insoluble monomers contain alkyl groups containing about 4 to 12 carbon atoms.

10. The electrode according to claim 9 wherein said water insoluble monomers are selected from the group consisting of alkyl acrylates, alkyl methacrylates and alkyl vinyl ethers.

11. The electrode according to claim 10 wherein said water insoluble monomers are selected from the group consisting of -butyl acrylate, 2-ethyl hexyl methacrylate, -octyl acrylate, butyl acrylate and lauryl methacrylate.

12. The electrode according to claim 8 wherein said water soluble monomers are selected from the group consisting of acrylic acid and methacrylic acid.

13. The electrode according to claim 12 wherein said water insoluble monomer is iso-octyl acrylate.

* * * * *